United States Patent
Lin et al.

(10) Patent No.: US 10,520,363 B2
(45) Date of Patent: Dec. 31, 2019

(54) RAMAN DETECTING CHIP FOR THIN LAYER CHROMATOGRAPHY AND METHOD FOR SEPARATING AND DETECTING AN ANALYTE

(71) Applicants: INDUSTRIAL TECHNOLOGY RESEARCH INSTITUTE, Hsinchu (TW); NATIONAL TSING HUA UNIVERSITY, Hsinchu (TW)

(72) Inventors: Ding-Zheng Lin, Taipei (TW); Ta-Jen Yen, Zhubei (TW); Bi-Shen Lee, New Taipei (TW); Chih-Hao Huang, Kaohsiung (TW)

(73) Assignees: INDUSTRIAL TECHNOLOGY RESEARCH INSTITUTE, Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/966,776

(22) Filed: Apr. 30, 2018

(65) Prior Publication Data
US 2018/0245981 A1 Aug. 30, 2018

Related U.S. Application Data

(63) Continuation-in-part of application No. 15/394,045, filed on Dec. 29, 2016, now Pat. No. 10,012,625.

(Continued)

(30) Foreign Application Priority Data

Nov. 21, 2016 (TW) .............................. 105138051 A
Nov. 21, 2017 (TW) .............................. 106140275 A

(51) Int. Cl.
*G01J 3/44* (2006.01)
*G01N 21/65* (2006.01)
(Continued)

(52) U.S. Cl.
CPC ........ *G01J 3/4412* (2013.01); *G01N 15/0211* (2013.01); *G01N 21/65* (2013.01);
(Continued)

(58) Field of Classification Search
CPC ...................................................... G01N 21/658
See application file for complete search history.

(56) References Cited

U.S. PATENT DOCUMENTS 7,116,416 B1 * 10/2006 Boss ...................... B82Y 15/00
                                                       356/301
7,158,219 B2    1/2007 Li et al.
(Continued)

FOREIGN PATENT DOCUMENTS

CN       103620358 A      3/2014
CN       104422751 A      3/2015
(Continued)

OTHER PUBLICATIONS

Chen, J., et al, "On-Chip Ultra-Thin Layer Chromatography and Surface Enhanced Raman Spectroscopy," Lab Chip, 2012, pp. 3096-3102.

(Continued)

*Primary Examiner* — Shawn Decenzo
(74) *Attorney, Agent, or Firm* — Birch, Stewart, Kolasch & Birch, LLP

(57) ABSTRACT

A Raman detecting chip for thin layer chromatography and a method for separating and detecting an analyte are provided. The Raman detecting chip for thin layer chromatography includes a silicon substrate. The silicon substrate includes a first portion, a second portion and a plurality of silicon nanowires disposed on the first portion, wherein each silicon nanowire has a top surface and a sidewall. A metal layer covers the top surface and at least a part of the sidewall of the silicon nanowire, wherein the silicon nanowire has a (Continued)

length L from 5 µm to 15 µm. The ratio between the length L1 of the side wall covered by the metal layer and the length L of the silicon nanowire is from 0.2 to 0.8.

9 Claims, 20 Drawing Sheets

Related U.S. Application Data

(60) Provisional application No. 62/274,938, filed on Jan. 5, 2016.

(51) Int. Cl.
    *G01N 30/95* (2006.01)
    *G01N 30/92* (2006.01)
    *G01N 15/02* (2006.01)
    *B82Y 35/00* (2011.01)

(52) U.S. Cl.
    CPC ........... *G01N 21/658* (2013.01); *G01N 30/92* (2013.01); *G01N 30/95* (2013.01); *B82Y 35/00* (2013.01)

(56) References Cited

U.S. PATENT DOCUMENTS

| | | | |
|---|---|---|---|
| 7,400,395 B2 | 7/2008 | Chan et al. | |
| 7,483,130 B2* | 1/2009 | Baumberg | G01N 21/658 356/301 |
| 7,738,096 B2 | 6/2010 | Zhao et al. | |
| 7,880,876 B2 | 2/2011 | Zhao et al. | |
| 7,940,387 B2 | 5/2011 | Dluhy et al. | |
| 8,107,070 B2 | 1/2012 | Zhao et al. | |
| 8,314,932 B2 | 11/2012 | Ou et al. | |
| 8,358,407 B2 | 1/2013 | Hu et al. | |
| 8,358,408 B2* | 1/2013 | Wu | G01N 21/658 356/301 |
| 8,547,549 B2 | 10/2013 | Kuo et al. | |
| 8,687,186 B2* | 4/2014 | Wang | B82Y 15/00 356/301 |
| 8,767,202 B2* | 7/2014 | Schmidt | G01N 21/658 356/301 |
| 8,810,789 B2* | 8/2014 | Zhao | G01J 3/4412 356/301 |
| 8,898,811 B2 | 11/2014 | Jen et al. | |
| 8,953,159 B2* | 2/2015 | Cunningham | G02B 1/005 356/301 |
| 9,127,984 B2* | 9/2015 | Tseng | G01J 3/44 |
| 9,322,708 B2* | 4/2016 | Yamada | G01N 21/65 |
| 9,410,949 B2* | 8/2016 | Singamaneni | B82Y 5/00 |
| 2006/0050280 A1* | 3/2006 | Wei | G01B 11/303 356/451 |
| 2008/0117423 A1* | 5/2008 | Ogawa | G01N 21/554 356/445 |
| 2008/0180662 A1* | 7/2008 | Wang | G01J 3/44 356/301 |
| 2010/0210029 A1* | 8/2010 | Meinhart | G01N 21/05 436/168 |
| 2011/0037976 A1 | 2/2011 | Zhao et al. | |
| 2012/0081703 A1* | 4/2012 | Moskovits | G01N 21/658 356/301 |
| 2013/0128265 A1* | 5/2013 | Zhao | G01J 3/4412 356/301 |
| 2013/0169960 A1* | 7/2013 | Cunningham | G01N 21/658 356/301 |
| 2014/0125976 A1 | 5/2014 | Kim et al. | |
| 2014/0127402 A1* | 5/2014 | Long | G01N 33/18 427/162 |
| 2014/0198314 A1* | 7/2014 | Li | G01N 21/658 356/301 |
| 2014/0209683 A1* | 7/2014 | Schultz | B82Y 30/00 235/454 |
| 2014/0218727 A1* | 8/2014 | Li | G01N 21/658 356/301 |
| 2014/0268128 A1* | 9/2014 | Wang | G01N 21/658 356/301 |
| 2015/0050556 A1 | 2/2015 | Liu et al. | |
| 2015/0065390 A1* | 3/2015 | Bratkovski | B01L 3/5088 506/12 |
| 2015/0131092 A1* | 5/2015 | Sakagami | G01N 21/658 356/301 |
| 2015/0157261 A1* | 6/2015 | Sakagami | G01N 21/658 600/476 |
| 2016/0003748 A1* | 1/2016 | Gibson | G01N 21/21 356/301 |
| 2016/0146736 A1* | 5/2016 | Chen | G01N 21/658 356/301 |
| 2016/0169886 A1* | 6/2016 | Chou | G01N 33/54393 506/9 |
| 2016/0245754 A1* | 8/2016 | Xin | B82Y 10/00 |
| 2016/0258867 A1* | 9/2016 | Chou | G01N 21/6452 |
| 2017/0184584 A1* | 6/2017 | Lin | G01N 33/54393 |
| 2017/0212106 A1* | 7/2017 | Linke | B01L 3/502761 |
| 2017/0254754 A1* | 9/2017 | Gibson | G01N 21/21 |
| 2017/0315058 A1* | 11/2017 | Zhou | G01N 21/648 |

FOREIGN PATENT DOCUMENTS

| | | |
|---|---|---|
| CN | 104897638 A | 9/2015 |
| CN | 104937391 A | 9/2015 |
| CN | 105259158 A | 1/2016 |
| TW | I485389 B | 5/2015 |
| WO | WO 2013/040782 A1 | 3/2013 |

OTHER PUBLICATIONS

Chinese Office Action for Appl. No. 201611186111.1 dated Dec. 24, 2018.

Freye, C.E., et al, "Surface Enhanced Raman Scattering Imaging of Developed Thin-Layer Chromatography Plates," ACS Publications, 2013, vol. 85, pp. 3991-3398.

Tang, H., et al, "Arrays of Cone-Shaped ZnO Nanorods Decorated with Ag Nanoparticles as 3D Surface-Enhanced Raman Scattering Substrates for Rapid Detection of Trace Polychlorinated Biphenyls," Adv. Funct. Mater., 2012, vol. 22, pp. 218-224.

Zhu, C., et al, "ZnO-nanotaper array sacrificial templated synthesis of noble-metal building-block assembled nanotube arrays as 3D SERS-substrates," Nano Research, 2015, vol. 8, No. 3, pp. 957-966.

Caudin, J.P., et al, "Coupling FT Raman and FT SERS microscopy with TLC plates for in situ identification of chemical compounds," Spectrochimica Acta Part A, 1995, vol. 51, pp. 1977-1983.

Chang et al., "A Wafer-Scale Backplane-Assisted Resonating Nanoantenna Array SERS Device Created by Tunable Thermal Dewetting Nanofabrication," Nanotechnology, vol. 25, Mar. 14, 2014, pp. 1-9 (10 pages total).

Matejka, P., et al, "Near-Infrared Surface-Enhanced Raman Scattering Spectra of Heterocyclic and Aromatic Species Adsorbed on TLC Plates Activated with Silver," Applied Spectroscopy, 1996, vol. 50, No. 3, pp. 409-414.

Oh et al., "Glass Nanopillar Arrays with Nanogap-Rich Silver Nanoislands for Highly Intense Surface Enhanced Raman Scattering," Advanced Materials, vol. 24, 2012 (published online Mar. 27, 2012), pp. 2234-2237.

Seol et al., "A Nanoforest Structure for Practical Surface-Enhanced Raman Scattering Substrates," Nanotechnology, vol. 23, Feb. 6, 2012, pp. 1-7 (8 pages total).

Taiwanese Office Action for Appl. No. 105138051 dated Nov. 8, 2017.

Takei et al., "TLC-SERS Plates with a Built-In SERS Layer Consisting of Cap-Shaped Noble Metal Nanoparticles Intended for Environmental Monitoring and Food Safety Assurance," Journal of Nanomaterials, vol. 2015, Article ID 316189, 2015, pp. 1-9 (10 pages total).

Zhang et al., "Large-Area Silver-Coated Silicon Nanowire Arrays for Molecular Sensing Using Surface-Enhanced Raman Spectroscopy," Advanced Functional Materials, vol. 18, 2008, pp. 2348-2355.

(56) References Cited

OTHER PUBLICATIONS

Zhang et al., "Thin Layer Chromatography Coupled with Surface-Enhanced Raman Scattering as a Facile Method for On-Site Quantitative Monitoring of Chemical Reactions," Analytical Chemistry, vol. 86, Jun. 30, 2014, pp. 7286-7292.

* cited by examiner

RAMAN DETECTING CHIP FOR THIN LAYER CHROMATOGRAPHY AND METHOD FOR SEPARATING AND DETECTING AN ANALYTE

CROSS REFERENCE TO RELATED APPLICATIONS

This application is a Continuation-In-Part of pending U.S. patent application Ser. No. 15/394,045, filed Dec. 29, 2016, which claims the benefit of U.S. Provisional Application No. 62/274,938 filed on Jan. 5, 2016, and claims priority from, Taiwan Application Serial Number 105138051, filed on Nov. 21, 2016 and entitled "Raman detecting chip for thin layer chromatography and method for separating and detecting an analyte", the entirety of which is incorporated by reference herein.

The application is based on, and claims priority from, Taiwan Application Serial Number 106140275, filed on Nov. 21, 2017, the disclosure of which is hereby incorporated by reference herein in its entirety.

TECHNICAL FIELD

The technical field relates to a Raman detecting chip for thin layer chromatography and method for separating and detecting an analyte.

BACKGROUND

A Raman scattering spectrum has the advantages of fingerprint specificity and multi-domain applications, and thus it is widely applied in biological sensing, pharmaceuticals, environmental monitoring, identification, and health monitoring. However, the detection sensitivity is low due to the weak Raman scattering signal strength and interference from other compounds when performing a qualitative and quantitative analysis utilizing the Raman spectroscopy.

Therefore, a novel detection system for extracting the Raman scattering signal and eliminating the interference signal is desired so as to address the aforementioned problems.

SUMMARY

Embodiments of the disclosure provide a Raman detecting chip for thin layer chromatography. The Raman detecting chip for thin layer chromatography of the disclosure includes a silicon substrate and a metal layer. The silicon substrate includes a first portion, a second portion and a plurality of silicon nanowires disposed on the first portion, wherein each silicon nanowire has a top surface and a sidewall. The metal layer covers the top surface and at least a part of the sidewall of the silicon nanowire, wherein the silicon nanowire has a length L from 5 µm to 15 µm.

Embodiments of the disclosure provide a method for separating and detecting an analyte. The method for separating and detecting an analyte of the disclosure includes providing the aforementioned Raman detecting chip for thin layer chromatography; providing a sample, wherein the sample includes a solvent and at least one compound; spotting the sample on the aforementioned Raman detecting chip for thin layer chromatography; separating the sample by a thin layer chromatography process to obtain at least one analysis spot; and analyzing the analysis spot via surface enhanced Raman scattering spectroscopy.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
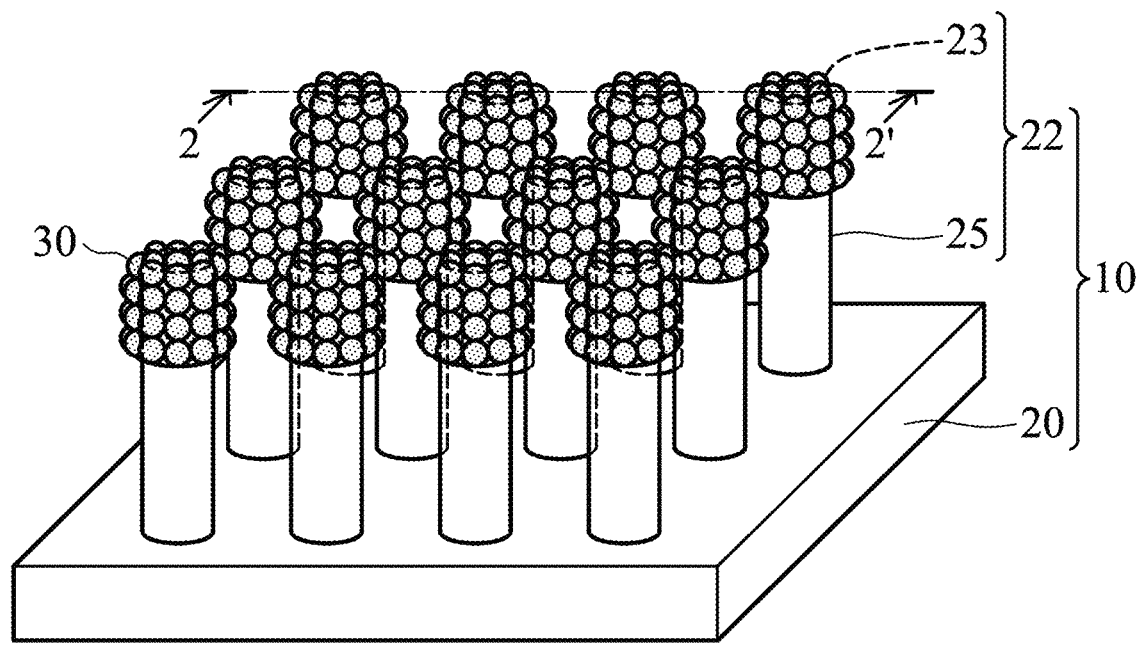
FIG. 1 is a schematic view of the Raman detecting chip for thin layer chromatography according to an embodiment of the disclosure.

The Raman detecting chip for thin layer chromatography and the method for separating and detecting an analyte of the disclosure are described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. In the drawings, the size, shape, or thickness of some of the elements may be exaggerated and not drawn in scale for illustrative purposes. The disclosure will be described with respect to particular embodiments and with reference to certain drawings but the disclosure is not limited thereto.

The disclosure provides a Raman detecting chip for thin layer chromatography and a method for separating and detecting an analyte. According to embodiments of the disclosure, the Raman detecting chip for thin layer chromatography can enable rapid separation and eliminate background interference due to the silicon nanowire having the specific length of the silicon substrate. In addition, the Raman signal detected by the Raman detecting chip of the disclosure can be enhanced due to the metal layer which covers a part of the surface of the silicon nanowire. As a result, the effects of the thin layer chromatography and surface enhanced Raman scattering spectroscopy can be achieved, simultaneously, resulting in efficiently reducing background interference and increasing detectability.

FIG. 1 is a schematic view of the Raman detecting chip for thin layer chromatography according to an embodiment of the disclosure. The Raman detecting chip for thin layer chromatography 100 includes a silicon substrate 10, wherein the silicon substrate 10 consists of a first portion 20 and a plurality of silicon nanowires 22 disposed on the first portion 20. Each silicon nanowire 22 can have a top surface 23 and a sidewall 25. A metal layer 30 can cover the top surface 23 and at least a part of the sidewall 25 of the silicon nanowire 22. The metal layer can consist of a plurality of metal particles. According to embodiments of the disclosure, suitable materials of the metal particles can be silver, gold, aluminum, copper, tin, titanium, barium, platinum, cobalt, or a combination thereof. According to embodiments of the disclosure, the first portion 20 and the plurality of silicon nanowires 22 of the silicon substrate 10 are integrally formed.

Figure 2:
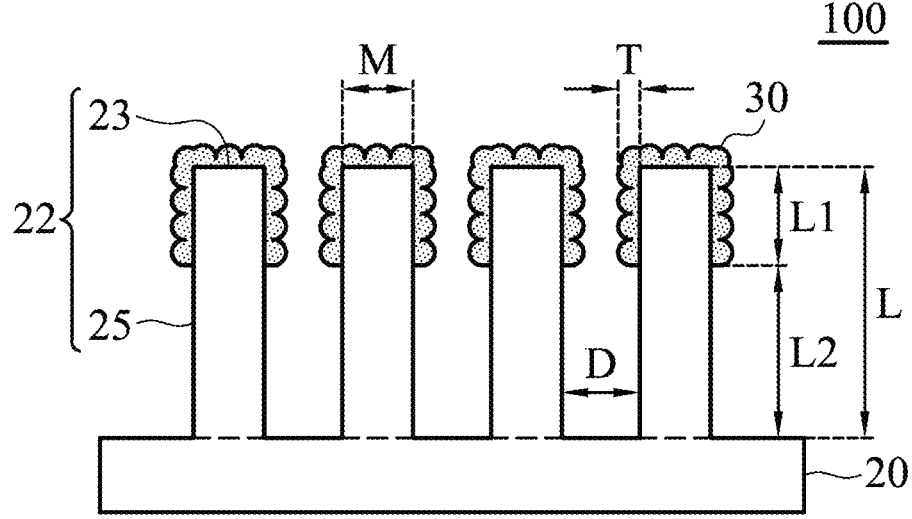
FIG. 2 is a cross-sectional view of the Raman detecting chip for thin layer chromatography as shown in FIG. 1 along the line 2-2'.

FIG. 2 is a cross-sectional view of the Raman detecting chip for thin layer chromatography as shown in FIG. 1 along the line 2-2'. As shown in FIG. 2, the silicon nanowire 22 can have a length L, wherein the length L can be from 5 μm to 15 μm (exhibiting the effects of thin layer chromatography). When the length L of the silicon nanowire 22 is too short, the adsorption force between the molecules of the analyte and the plurality of silicon nanowire 22 is greatly reduced, resulting in a longer separation distance, higher cost, and longer measurement time. Conversely, when the length L of the silicon nanowire 22 is too long, the adsorption force between the molecules of the analyte and the plurality of silicon nanowires 22 is greatly increased, resulting in the analyte not being able to be identified and isolated.

According to embodiments of the disclosure, as shown in FIG. 2, the top surface 23 of the silicon nanowire 22 can have a diameter M from about 50 nm to 200 nm. According to embodiments of the disclosure, a distance D between any two adjacent silicon nanowires (such as the distance between the side walls of any two adjacent silicon nanowires) is from about 50 nm to 200 nm. When the distance D is from about 100 nm to 200 nm, the short distance between the nano-particles of the metal layer disposed on the top surface of the two adjacent silicon nanowires may enhance the Raman scattering effect. Furthermore, the short distance can ensure that the adsorption force between the molecules of the analyte and the plurality of silicon nanowires 22 is sufficient. In addition, According to embodiments of the disclosure, the metal layer 30 can have a thickness T from about 20 nm to 100 nm. When the thickness T of the metal layer 30 is from about 20 nm to 100 nm, the short distance between the nano-particles of the metal layer disposed on the top surface of the two adjacent silicon nanowires may enhance the Raman scattering effect.

Figure 3:
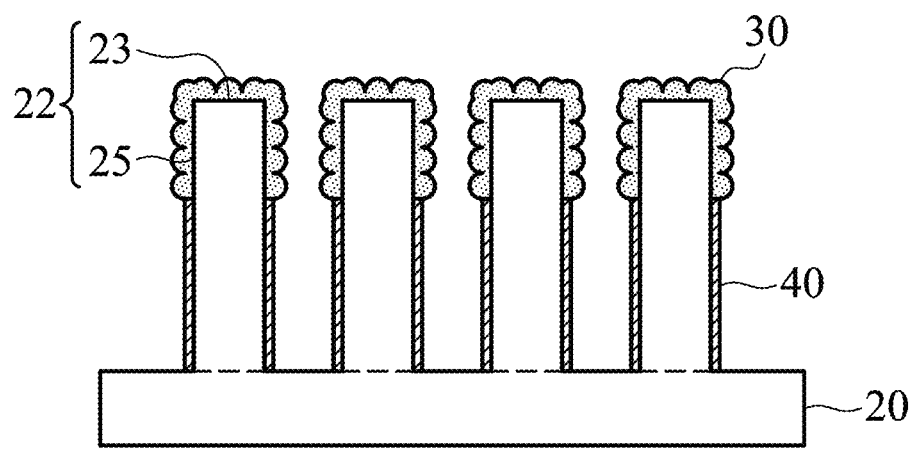
FIGS. 3-5 are cross-sectional views of the Raman detecting chips for thin layer chromatography according to other embodiments of the disclosure.

In addition, as shown in FIG. 2, the metal layer 30 completely covers top surface 23 of the nanowire 22, and further extends to the side wall 25 of the nanowire 22, such that the metal layer 30 covers a part of the side wall 25 of the silicon nanowire 22. As a result, a part of the side wall 25 of the silicon nanowire 22 is not covered by the metal layer 30. According to some embodiments of the disclosure, the ratio L1/L between the length L1 of the side wall covered by the metal layer 30 and the length L of the silicon nanowire 22 is from about 0.2 to 0.8. For example, the ratio L1/L between the length L1 of the side wall covered by the metal layer 30 and the length L of the silicon nanowire 22 can be from about 0.3 to 0.74. When the area of the silicon nanowire 22 covered by the metal layer 30 is too small (i.e. the ratio L1/L is too low), the enhanced Raman scattering effect would be confined to the superficial region of the silicon nanowire. Conversely, when the area of the silicon nanowire 22 covered by the metal layer 30 is too large (i.e. the ratio L1/L is too high), the adsorption force between the molecules of the analyte and the plurality of silicon nanowires 22 is greatly reduced, resulting in a longer separation distance, higher cost, and longer measurement time. On the other hand, as shown in FIG. 2, the ratio L2/L between the length L2 of the side wall 25, which is not covered by the metal layer 30, and the length L of the silicon nanowire 22 can be from about 0.2 to 0.8 (such as from about 0.26 to 0.7). According to embodiments of the disclosure, the Raman detecting chip for thin layer chromatography of the disclosure can further include a modification layer 40 disposed on the side wall 25 which is not covered by the metal layer 30, as shown in FIG. 3. The modification layer 40 can be a material which increases or reduces the adsorption force between the molecules of the analyte and the silicon nanowire. For example, the modification layer 40 can be formed on the side wall 25, which is not covered by the metal layer 30, of the silicon nanowire 22, and the modification layer 40 can be a silicon oxide layer, silicon nitride layer, aluminum oxide layer, or a functional modification material which adjusts the polarity of the silicon nanowire.

Figure 4:
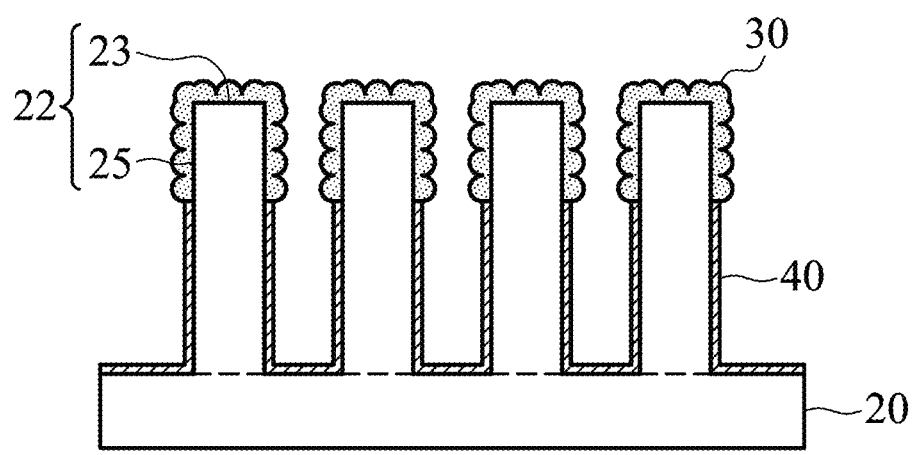

According to embodiments of the disclosure, the modification layer 40 can be formed on the side wall 25 which is not covered by the metal layer 30, and further formed on the surface of the first portion 20 of the silicon substrate 10 (i.e. the surface, which is not covered by the silicon nanowires 22, of the first portion 20), as shown in FIG. 4.

Figure 5:
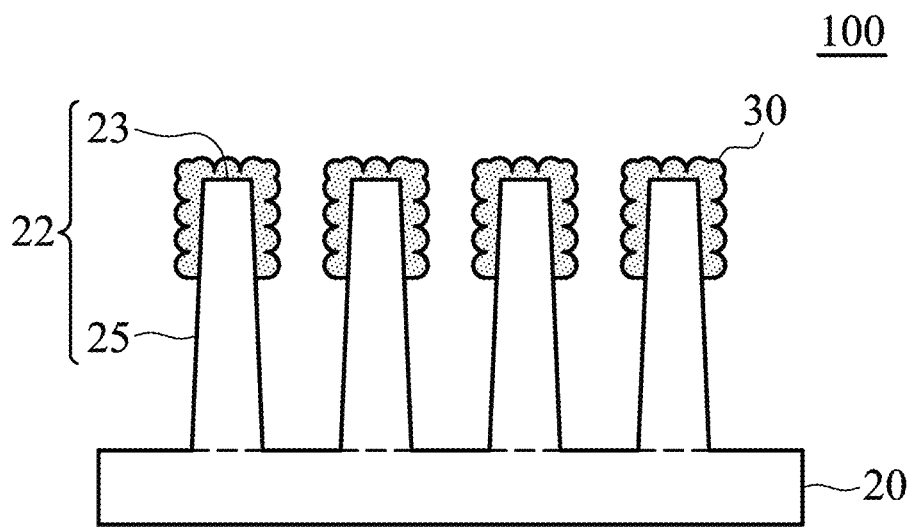

According to some embodiments of the disclosure, the side wall 25 of the nanowire 22 can be a slanted side wall, as shown in FIG. 5. Namely, the side wall 25 of the nanowire 22 is not perpendicular to the first portion 20. The silicon nanowires 22 are apt to be substantially perpendicular to the first portion 20 of the silicon substrate 10 when the side wall 25 of the nanowire 22 is a slanted side wall.

Figure 6A:
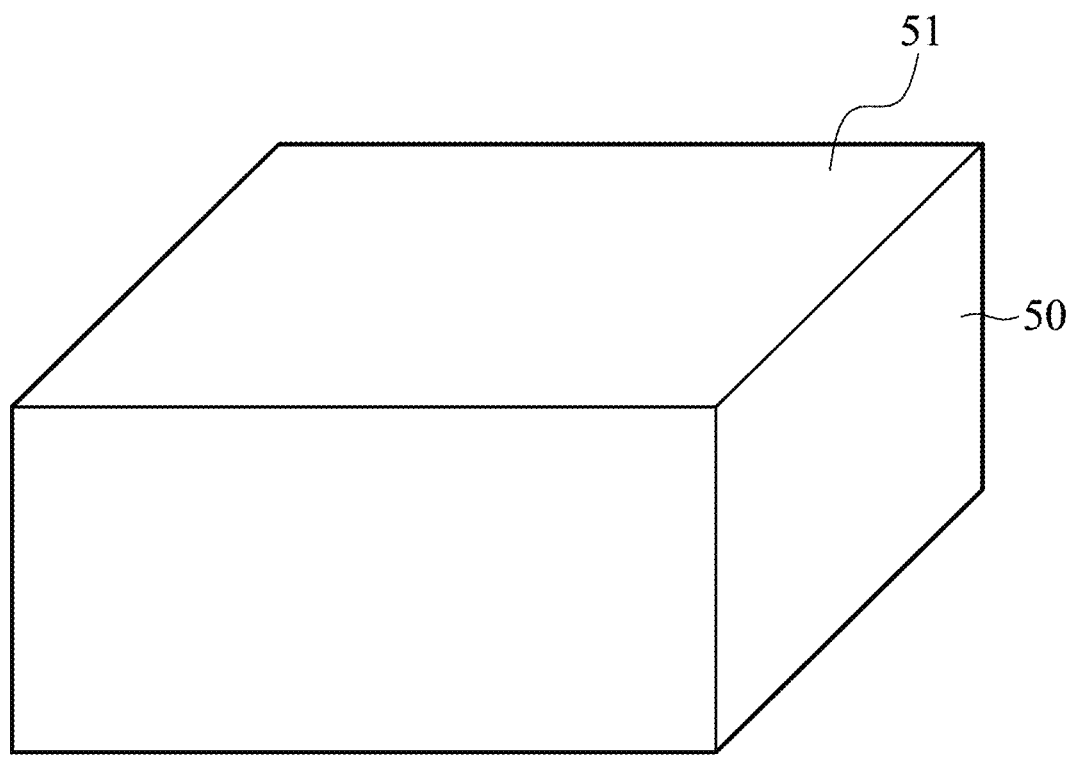
FIGS. 6A-6D are schematic views showing a fabrication process of the silicon substrate according to embodiments of the disclosure.
Figure 6B:
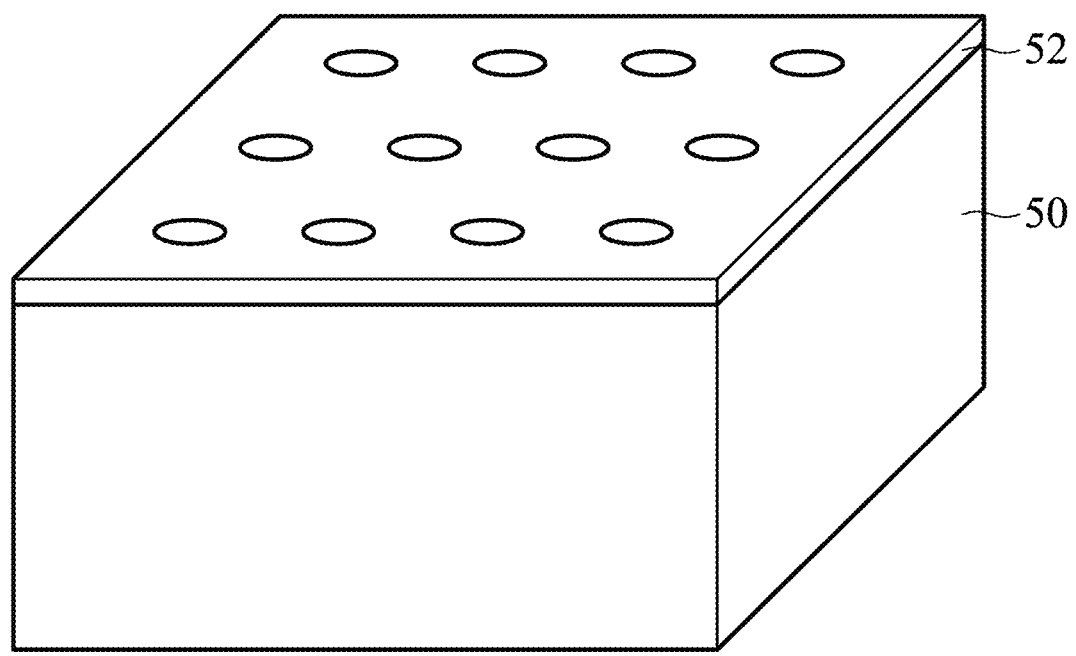
Figure 6C:
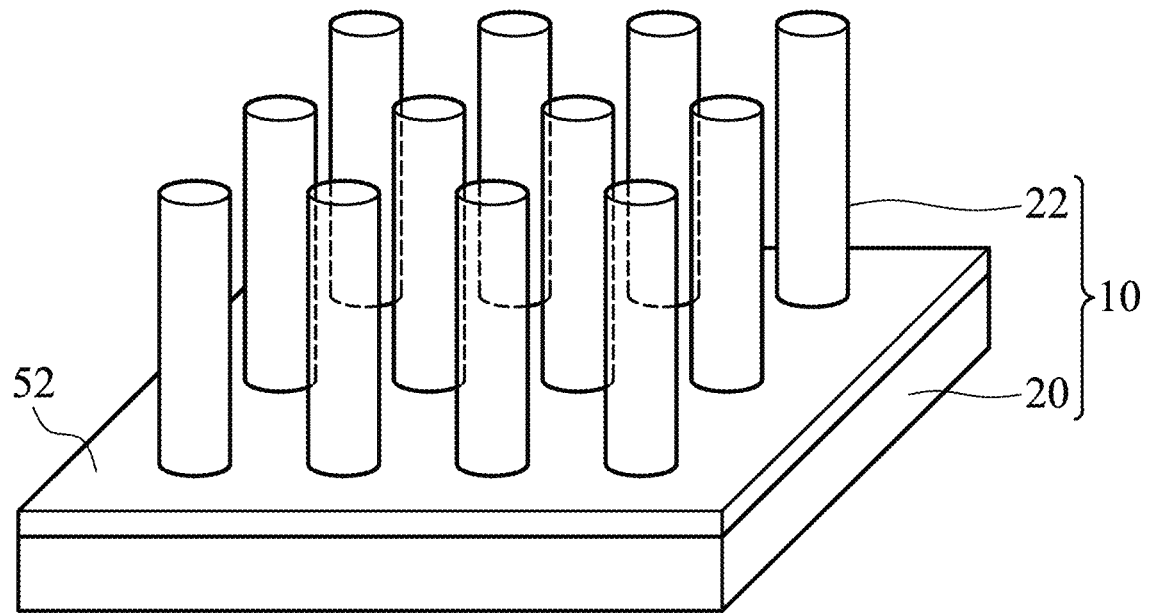
Figure 6D:
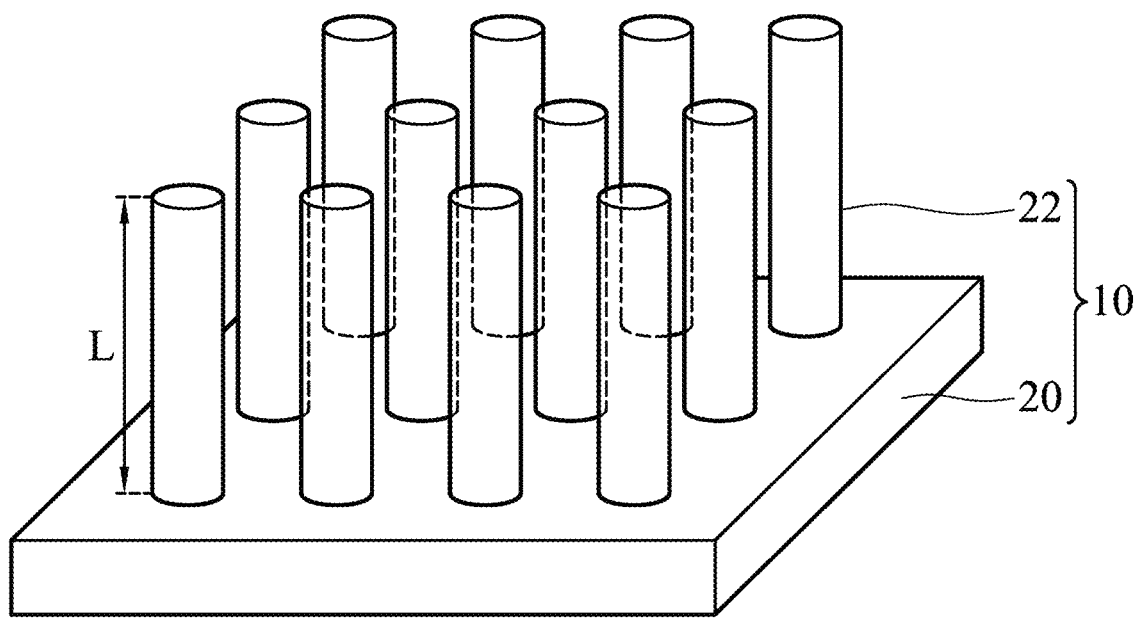

According to embodiments of the disclosure, the fabrication process of the Raman detecting chip for thin layer chromatography of the disclosure can include the following steps. First, a silicon chip 50 (such as a single-crystalline silicon chip) with a specific size is provided, as shown in FIG. 6A. For example, the single-crystalline silicon chip 50 can have a length from about 20 mm to 25 mm, a width from about 10 mm to 15 mm, and a thickness from about 500 m to 1 mm. Next, the single-crystalline silicon chip 50 is immersed in a first solution (including silver nitrate ($AgNO_3$) and hydrofluoric acid (HF)) for a first time period (such as about 5-10 seconds), and thus a network-shaped silver nano-scale pattern 52 is formed on the top surface 51 of the single-crystalline silicon chip 50, as shown in FIG. 6B. Next, the top surface 51 of the single-crystalline silicon chip 50 is separated from the first solution. Next, the top surface 51 of the single-crystalline silicon chip 50 (having a network-shaped silver nano-scale pattern 52) is immersed in a second solution (including hydrogen peroxide ($H_2O_2$) and hydrofluoric acid (HF)) for a second time period (such as about 40 minutes), such that the single-crystalline silicon chip 50 is subjected to a metal assisted chemical etching (MACE) process. In the metal assisted chemical etching process, the surface, which is covered by the network-shaped silver nano-scale pattern 52, of the single-crystalline silicon chip 50 is etched downward, as shown in FIG. 6C. Next, the network-shaped silver nano-scale pattern 52 is removed, thereby obtaining the silicon substrate 10 consisting of the first portion 20 and the plurality of silicon nanowires 22 as shown in FIG. 6D. In addition, the length L of the nanowire 22 can be controlled by increasing or reducing the time period of the metal assisted chemical etching process. For example, the length L of the nanowire 22 and the time period of the metal assisted chemical etching process are in direct proportion. Finally, the silicon substrate 10 is separated from the second solution, and then the silicon substrate 10 is immersed in a third solution for a third time period (such as about 30-240 seconds) such that the metal layer (a silver layer) is formed to cover the top surface 23 of the silicon nanowire 22 and further extend towards the side wall 25 to cover a part of the side wall 25 of the silicon nanowire 22. Therefore, the Raman detecting chip for thin layer chromatography 100 as shown in FIG. 1 is obtained. Herein, the length L1 of the silicon nanowire 22 covered by the metal layer 30 can be controlled by increasing or reducing the third period of time. For example, the length L1 of the silicon nanowire 22 covered by the metal layer 30 and the third period of time are in direct proportion.

Figure 7:
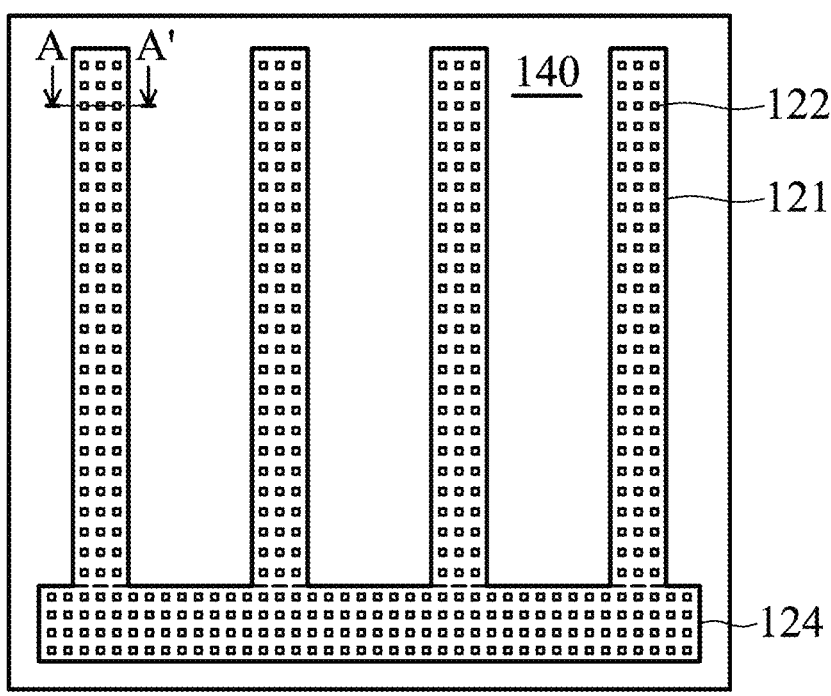
FIG. 7 is a schematic view of the patterned Raman detecting chip for thin layer chromatography according to an embodiment of the disclosure.

According to embodiments of the disclosure, the disclosure also provides a patterned Raman detecting chip. FIG. 7 is a top view of the patterned Raman detecting chip 200 of the disclosure. As shown in FIG. 7, the patterned Raman detecting chip 200 includes a silicon substrate 110, wherein the silicon substrate 110 consists of a first portion 120 (i.e. structural portion), a second portion 140 (i.e. planar portion), and a plurality of silicon nanowires 122 disposed on the first portion. It should be noted that the plurality of silicon nanowires 122 are only disposed on the first portion 120, and no silicon nanowire 122 is disposed on the second portion 140. Furthermore, the first portion 120 has a plurality of (such as at least two) sub-regions 121 separated from each other, wherein the two sub-regions 121 can be a plurality of (such as at least two) strip-shaped regions which have longitudinal axes parallel to each other. Furthermore, the first portion 120 can include a base region 124, wherein the sub-regions 121 are in direct contact with the base region 124. According to embodiments of the disclosure, the first portion 120, the second portion 140 and the plurality of silicon nanowires 122 of the silicon substrate 110 are integrally formed.

Figure 8:
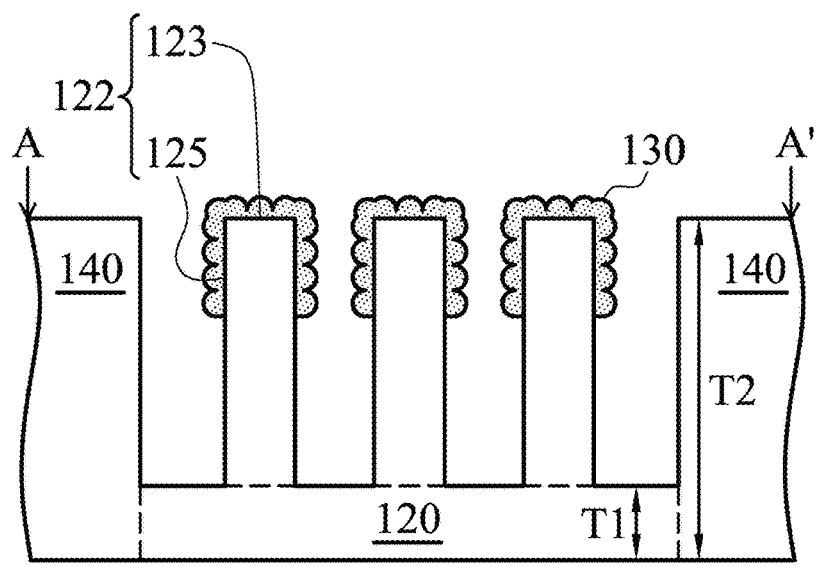
FIG. 8 is a cross-sectional view of the patterned Raman detecting chip for thin layer chromatography as shown in FIG. 7 along line A-A'.

FIG. 8 is a cross-sectional view of the patterned Raman detecting chip 200 as shown in FIG. 7 along line A-A'. Each silicon nanowire 122 can have a top surface 123 and a sidewall 125. A metal layer 130 can cover the top surface 123 and at least a part of the sidewall 125 of the silicon nanowire 22. Furthermore, a modification layer is disposed on the side wall 125 of the silicon nanowire 122 which is not covered by the metal layer 130. The metal layer and the modification layer are defined as above. As shown in FIG. 8, the thickness T2 of the second portion 140 of the silicon substrate 110 is greater than the thickness T1 of the first portion 120. According to embodiments of the disclosure, when performing a thin layer chromatography process with the patterned Raman detecting chip, the separated compound can be confined in the strip-shaped region, thereby enhancing the Raman scattering signal strength. The plurality of (such as at least two) sub-regions 121 can be a plurality of (such as at least two) strip-shaped regions which have longitudinal axes parallel to each other. Furthermore, the first portion 120 can include a base region 124, wherein the sub-regions 121 are in direct contact with the base region 124.

Figure 9:
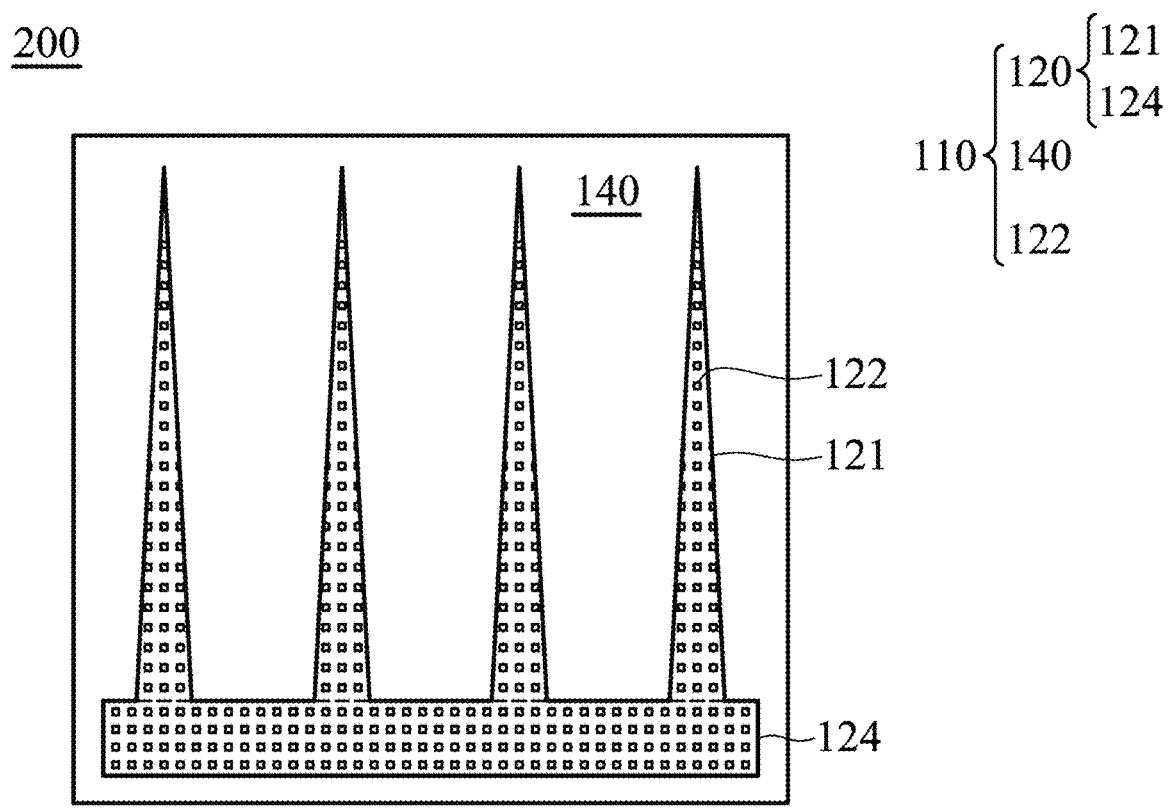
FIGS. 9 and 10 are schematic views of the patterned Raman detecting chip for thin layer chromatography according to other embodiments of the disclosure.

According to embodiments of the disclosure, as shown in FIG. 9, the plurality of (such as at least two) sub-regions 121 separated from each other of the patterned Raman detecting chip 200 can be a plurality of (such as at least two) triangle-shaped regions which have longitudinal axes parallel to each other. Furthermore, the first portion 120 can include a base region 124, wherein the triangle-shaped regions are in direct contact with the base region 124. The surface area of the triangle-shaped region is inversely proportional to the height of the triangle-shaped region. As a result, the separated compound can be further concentrated when the separated compound is located near the vertex of the triangle-shaped region, thereby enhancing the Raman scattering signal strength.

Figure 10:
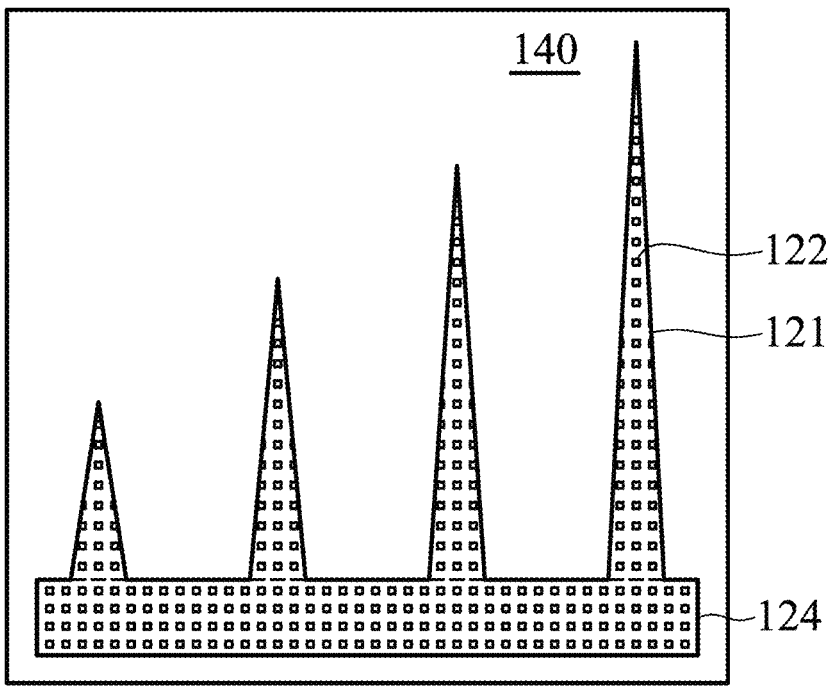

Furthermore, as shown in FIG. 10, the plurality of sub-regions 121 separated from each other of the patterned Raman detecting chip 200 can be a plurality of (such as at least two) triangle-shaped regions which have different height. As a result, according the separation distance of the desired compound, the triangle-shaped region having the specific height can be selected for detecting surface enhanced Raman scattering spectroscopy of the desired compound, thereby enhancing the Raman scattering signal strength.

Figure 11A:
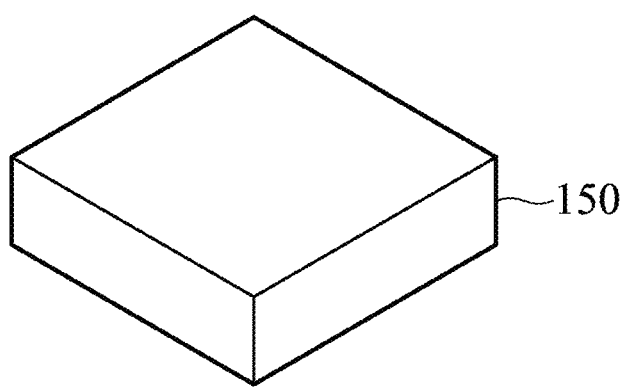
FIGS. 11A-11F are schematic views showing a fabrication process of the patterned Raman detecting chip for thin layer chromatography according to embodiments of the disclosure.
Figure 11B:
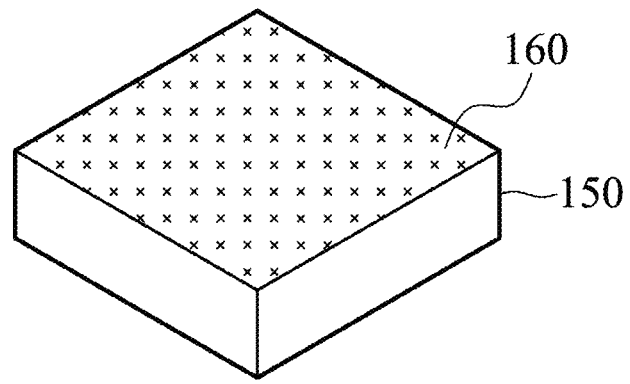

According to embodiments of the disclosure, the patterned Raman detecting chip can be prepared by following steps. First, a single-crystalline silicon chip 150 with a specific size is provided, as shown in FIG. 11A. For example, the single-crystalline silicon chip 150 can have a length from about 20 mm to 25 mm, a width from about 10 mm to 15 mm, and a thickness from about 500 μm to 1 mm. Next, a photoresist composition is coated on top surface of the single-crystalline silicon chip 150. After drying, a photoresist layer 160 is formed to completely cover the top surface of the single-crystalline silicon chip 150, as shown in FIG. 11B. Herein, the photoresist composition used for forming the photoresist layer 160 is unlimited and can be a positive photoresist composition. The photoresist layer 160 can have a thickness of from about 0.1 μm to 200 μm.

Figure 11C:
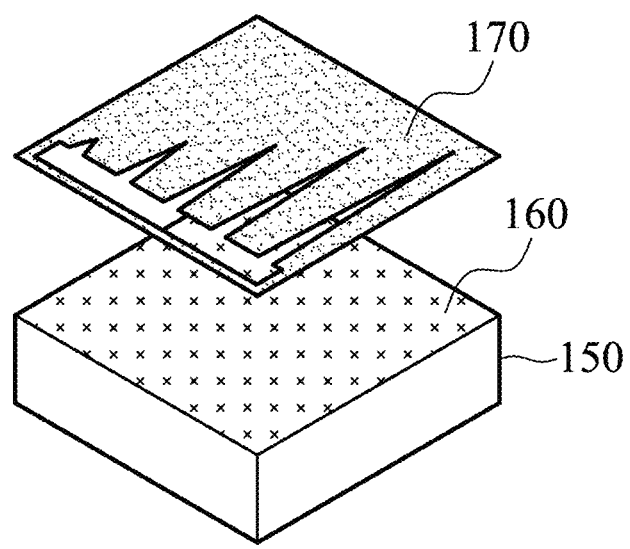
Figure 11D:
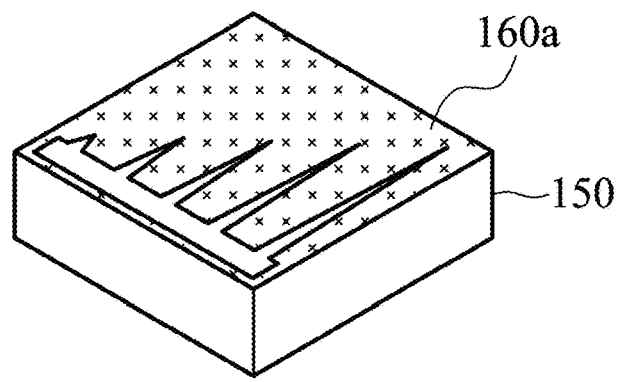

Next, the photoresist layer 160 is exposed through a photomask 170, as shown in FIG. 11C. Next, a development process is performed, thereby forming a patterned photoresist layer 160a, as shown in FIG. 11D. Herein, the top surface of the single-crystalline silicon chip 150, which is not covered by the photoresist layer 160a, is defined as a predetermined region of the plurality of silicon nanowires. Namely, the single-crystalline silicon chip 150 exposed by the patterned photoresist layer 160a is defined as a predetermined region of the first portion of the silicon substrate 110, and the single-crystalline silicon chip 150 covered by the patterned photoresist layer 160a is defined as a predetermined region of the second portion of the silicon substrate 110.

Figure 11E:
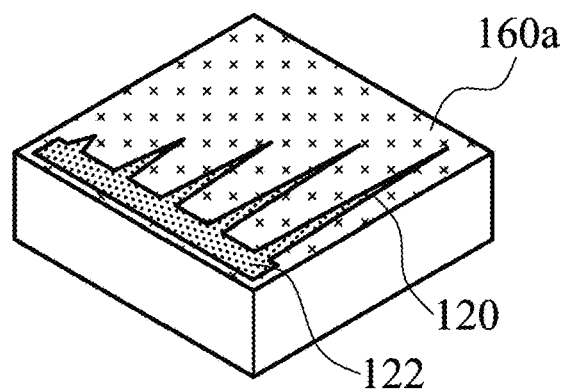
Figure 11F:
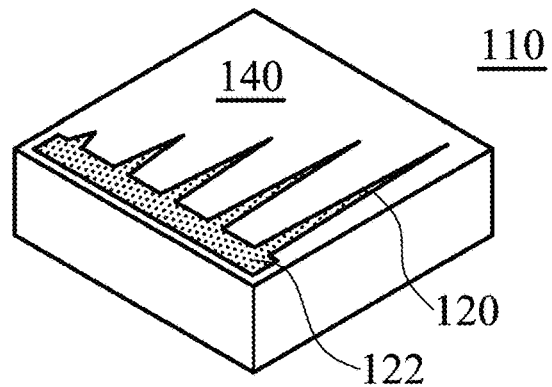

Next, the single-crystalline silicon chip 150 with the patterned photoresist layer 160a is immersed in a first solution including silver nitrate ($AgNO_3$) and hydrofluoric acid (HF) for a first time period (such as about 5-10 seconds), and thus a network-shaped silver nano-scale pattern is formed on the exposed top surface (i.e. the surface which is not covered by the patterned photoresist layer 160a) of the single-crystalline silicon chip 150. Next, the single-crystalline silicon chip 150 is separated from the first solution. Next, the single-crystalline silicon chip 150 (having a network-shaped silver nano-scale pattern on the surface thereof) is immersed in a second solution (including hydrogen peroxide ($H_2O_2$) and hydrofluoric acid (HF)) for a second time period (such as about 40 minutes), such that the single-crystalline silicon chip 150 is subjected to a metal assisted chemical etching (MACE) process. In the metal assisted chemical etching process, the surface, which is covered by the network-shaped silver nano-scale pattern, of the single-crystalline silicon chip 150 is etched downward. Next, the network-shaped silver nano-scale pattern is removed, and the formation of the first portion 120 is completed, as shown in FIG. 11E. Next, the patterned photoresist layer 160a is removed to expose the second portion 140, and the formation of the silicon substrate 110 of the patterned Raman detecting chip. Finally, the silicon substrate 110 is immersed in a third solution (including silver nitrate ($AgNO_3$)) for a third time period (such as about 30-240 seconds) such that the metal layer (a silver layer) is formed to cover the top surface of the silicon nanowire 122 and further extend towards the side wall to cover a part of the side wall of the silicon nanowire 122. Therefore, the patterned Raman detecting chip 200 as shown in FIG. 10 is obtained.

Figure 12A:
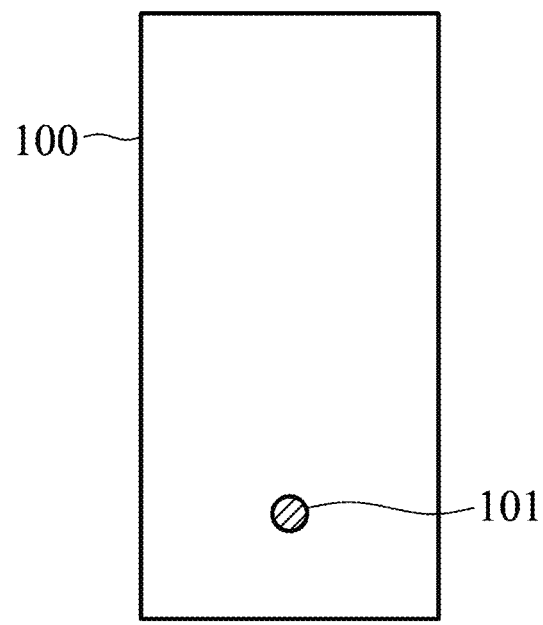
FIGS. 12A and 12B are schematic views showing a thin layer chromatography process employing the Raman detecting chip for thin layer chromatography according to an embodiment of the disclosure.
Figure 12B:
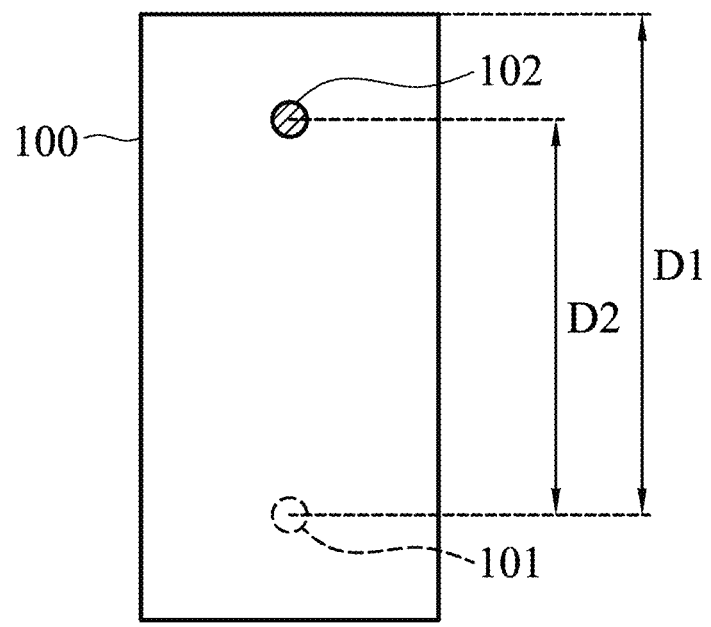

According to embodiments of the disclosure, the disclosure also provides a method for separating and detecting an analyte. The method includes the following steps. First, a Raman detecting chip for thin layer chromatography of the disclosure is provided. Next, a sample is provided, wherein the sample includes a solvent and at least one compound. Herein, the solvent can be a solvent which can be used to dissolve the compound. Next, the sample is spotted onto the Raman detecting chip for thin layer chromatography 100 to form a sample spot 101, as shown in FIG. 12A. Next, the compound of the sample is separated by thin layer chromatography process. Thus, at least one analysis spot 102 can be formed on the Raman detecting chip 100, as shown in FIG. 12B.

Finally, the analysis spot is analyzed via surface enhanced Raman scattering spectroscopy. In particular, the distance D1 is the distance that a developing solution travels up the Raman detecting chip 100, and the distance D2 is the distance between the analysis spot 102 and the sample spot 101. The retention factor (Rf) value may represent the quotient of D2 over D1 (i.e. Rf value is D2/D1). In the thin layer chromatography process, the Raman detecting chip for thin layer chromatography 100 is used as a stationary phase, and a developing solution (liquid) is used as a mobile phase. The developing solution is not limited and may be chosen according to the discretion of one skilled in the art. For example, the developing solution can include, but is not limited to, dichloromethane (DCM), methanol, ethyl ether, ethyl acetate (EA), n-hexane, acetone, chloroform, toluene, water, or a combination thereof.

According to embodiments of the disclosure, the method for separating and detecting an analyte can be performed with the pattern Raman detecting chip. The method includes providing the patterned Raman detecting chip and a sample, wherein the sample includes a solvent and at least one compound. In the thin layer chromatography process, the patterned Raman detecting chip for thin layer chromatography is used as a stationary phase, and a developing solution (liquid) is used as a mobile phase. In particular, the extension direction (longitudinal axis) of the strip-shaped regions or the triangle-shaped regions is parallel to the developing direction of the developing solution.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

First, a single-crystalline silicon chip (15 mm×25 mm) was provided. Next, the single-crystalline silicon chip was immersed in a solution including silver nitrate ($AgNO_3$) and hydrofluoric acid (HF)) for a first time period (about 10 seconds). In particular, a network-shaped silver pattern was formed on one surface of the single-crystalline silicon chip. Next, the single-crystalline silicon chip was separated from the solution, and then the single-crystalline silicon chip was immersed in a solution including hydrogen peroxide ($H_2O_2$) and hydrofluoric acid (HF) for a second time period (about 4 minutes), such that the single-crystalline silicon chip was subjected to a metal assisted chemical etching (MACE) process. After removing the network-shaped silver pattern, a silicon substrate having a plurality of silicon nanowires was obtained, wherein the average length L of the silicon nanowires was of about 1 μm. Next, the silicon substrate was immersed in a solution including silver nitrate (AgNO$_3$) for a third time period (about 120 seconds), and then a silver particle layer was formed to cover the top surface and a part of the side wall of the silicon nanowire. Therefore, Raman detecting chip (1) was obtained, wherein the ratio L1/L between the length L1 of the side wall covered by the silver particle layer and the length L of the silicon nanowire was about 0.74.

Example 2

Example 2 was performed in the same manner as in Example 1 except that the second time period was increased from 4 to 8 minutes, obtaining Raman detecting chip (2). In particular, the average length L of the silicon nanowires of Raman detecting chip (2) was of about 2 μm, and the ratio L1/L was of about 0.6.

Example 3

Example 3 was performed in the same manner as in Example 1 except that the second time period was increased from 4 to 20 minutes, obtaining Raman detecting chip (3). In particular, the average length L of the silicon nanowires of Raman detecting chip (3) was of about 5 μm, and the ratio L1/L was of about 0.46.

Example 4

Figure 13:
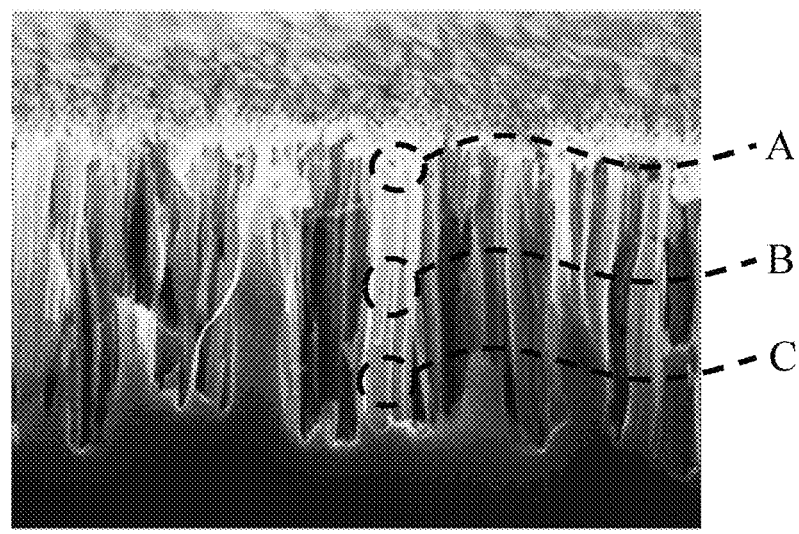
FIG. 13 is scanning electron microscope (SEM) photograph of a cross-sectional structure of the Raman detecting chip (4) as disclosed in Example 4.

Example 4 was performed in the same manner as in Example 1 except that the second time period was increased from 4 to 40 minutes, obtaining Raman detecting chip (4). In particular, the average length L of the silicon nanowires of Raman detecting chip (4) was of about 10 μm, and the ratio L1/L was of about 0.4. FIG. 13 is a scanning electron microscope (SEM) photograph of a cross-sectional structure of the Raman detecting chip (4) as disclosed in Example 4. The ratio of silver to silicon of regions A, B, and C shown in FIG. 13 were measured by energy dispersive spectroscopy (EDS), and the results are shown in Table 1.

TABLE 1

|  | ratio of silver to silicon (Ag/Si) |
| --- | --- |
| region A | 0.123 |
| region B | 0.118 |
| region C | 0.0012 |

As shown in Table 1, the silver particle layer is formed on the upper part of the silicon nanowire and is not formed on the lower part of the silicon nanowire.

Example 5

Example 5 was performed in the same manner as in Example 1 except that the second time period was increased from 4 to 60 minutes, obtaining Raman detecting chip (5). In particular, the average length L of the silicon nanowires of Raman detecting chip (5) was of about 15 μm, and the ratio L1/L was of about 0.37.

Example 6

Example 6 was performed in the same manner as in Example 1 except that the second time period was increased from 4 to 80 minutes, obtaining Raman detecting chip (6). In particular, the average length L of the silicon nanowires of Raman detecting chip (6) was of about 20 μm, and the ratio L1/L was of about 0.3.

Detection and Separation of Melamine by Means of Raman Detecting Chips

Example 7

Figure 14:
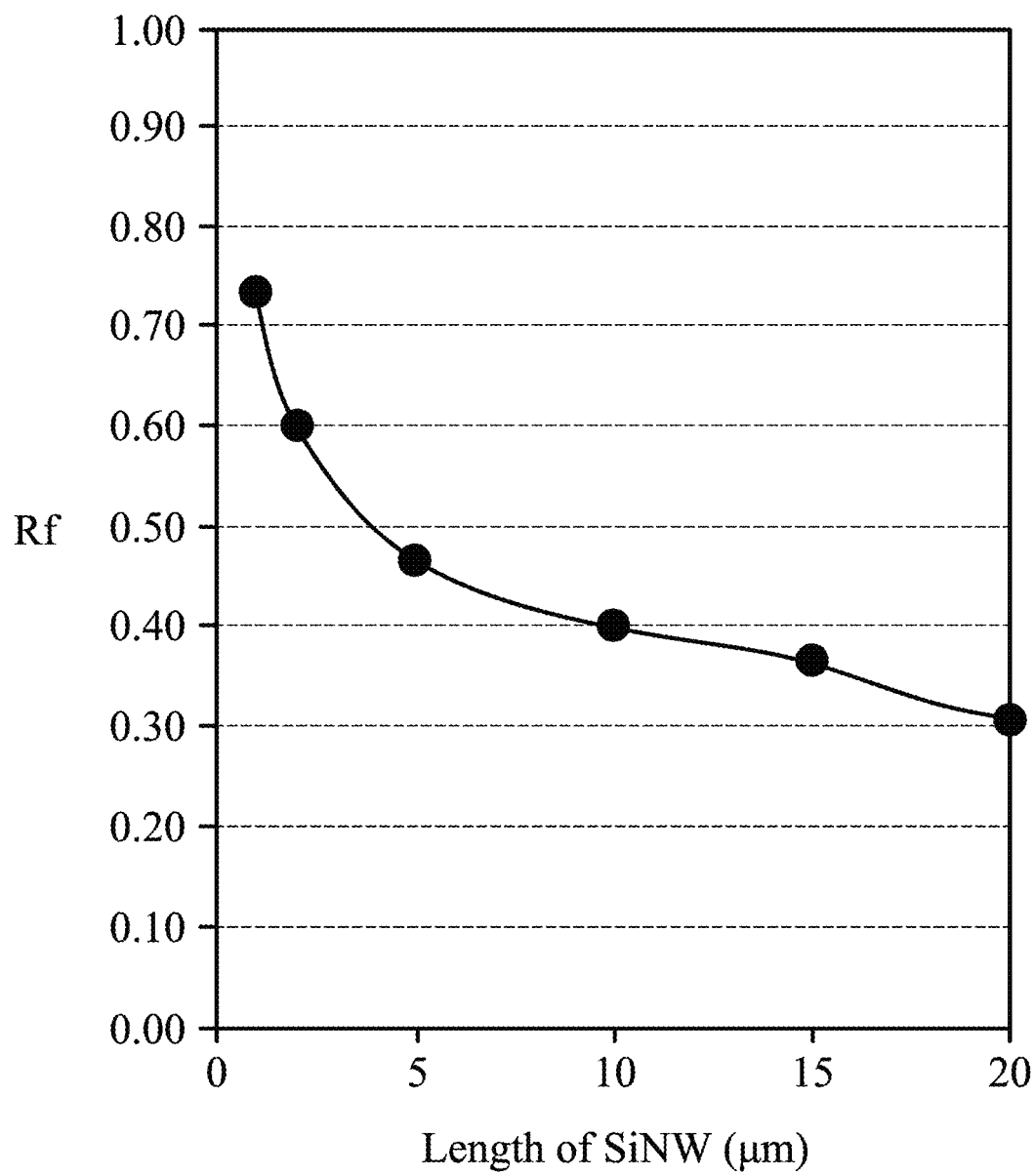
FIG. 14 is a graph plotting silicon nanowire length against retention factor (Rf) value in Examples 1-6.

First, a milk added to 50 ppm of melamine was provided and served as a sample. Next, the sample was applied to Raman detecting chips (1)-(6) with the Camag Linomat 5 sample applicator via air pressure. Next, Raman detecting chips (1)-(6) were disposed in developing tanks respectively, and the sample was developed with methanol serving as a developing solution. After developing, the Rf value of strongest melamine signal of Raman detecting chips (1)-(6) was determined by surface enhanced Raman scattering spectroscopy, and the results are shown in FIG. 14. In particular, the Raman detecting chip have several analysis spots arranged in developing direction, and each two adjacent analysis spots are separated by an interval of 1 mm.

As shown in FIG. 14, when the length L of the silicon nanowire of the Raman detecting chip is less than about 5 μm (such as 1 μm, or 2 μm), the adsorption force between the molecules of the analyte and the plurality of silicon nanowire is greatly reduced, resulting in a longer separation distance (relatively high Rf value), higher cost, and longer measurement time. When the length L of the silicon nanowire of the Raman detecting chip is greater than about 15 μm (such as 20 μm), the adsorption force between the molecules of the analyte and the plurality of silicon nanowire is greatly increased, resulting in the analyte not being apt to move with the developing solution, meaning that the separation distance is reduced (relatively low Rf value) and melamine is not identified and isolated. In addition, according to the results of Example 7, the Raman scattering signal strength of melamine is reduced when the separation distance is relatively low or high.

Example 8

Figure 15:
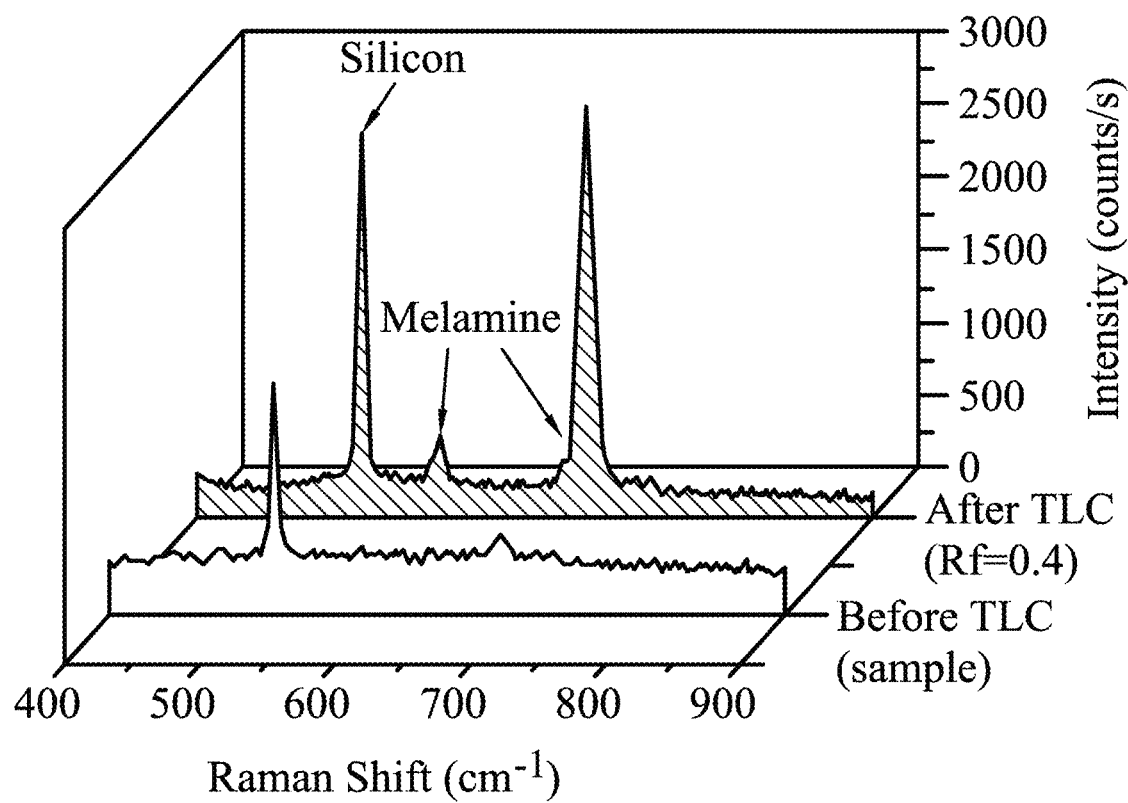
FIG. 15 is a Raman spectrum for detecting melamine surface enhanced Raman scattering spectroscopy employing the Raman detecting chip (4) as disclosed in Example 9.

First, a milk added to 30 ppm of melamine was provided and served as a sample. Next, the sample was applied to Raman detecting chip (4) with the Camag Linomat sample applicator (Camag Linomat 5) via air pressure. Next, the sample point was analyzed via surface enhanced Raman scattering spectroscopy, and the result is shown in FIG. 15. Next, Raman detecting chip (4) is disposed in developing tank, and the sample was developed with methanol serving as a developing solution. After developing, the Rf value of strongest melamine signal of Raman detecting chip (4) was determined by surface enhanced Raman scattering spectroscopy, and the results are shown in FIG. 15. In particular, the Raman detecting chip has several analysis spots arranged in the developing direction, and each two adjacent analysis spots are separated by an interval of 1 mm. As shown in FIG. 15, in comparison with the sample point (before developing), the Raman scattering signal strength of melamine in the analysis spot with an Rf value of 0.4 is ten times more than the Raman scattering signal strength of melamine in the sample point. It means that the melamine (small molecule) can be separated from the protein (large molecule) after developing and the interference caused by the protein occupying the detection area, resulting in enhancing the Raman scattering signal strength of melamine.

Example 9

Example 9 was performed in the same manner as in Example 8 except that the concentration of melamine was reduced from 30 to 5 ppm. In comparison with the sample point (before developing), the strongest Raman scattering signal strength of melamine in the analysis spot is five times more than the Raman scattering signal strength of melamine in the sample point. As a result, the Raman detecting chip of the disclosure can efficiently eliminate background interference and increase detectability even though the concentration of melamine was low.

Preparation of Patterned Raman Detecting Chip

Example 10

Figure 16:
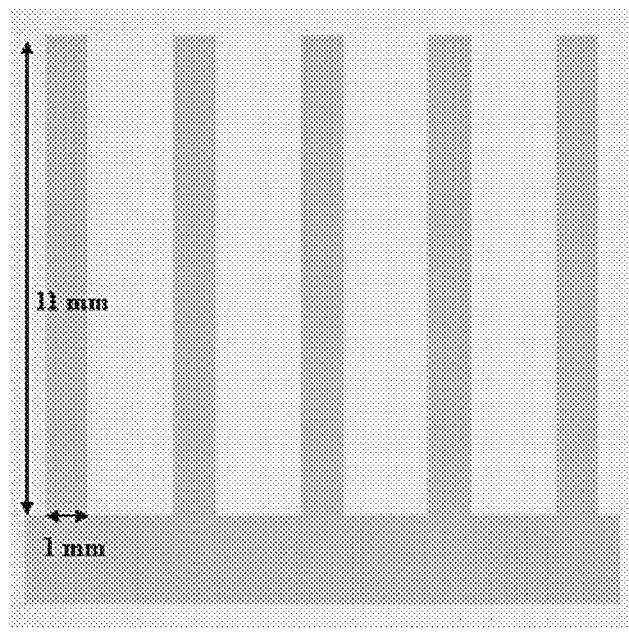
FIG. 16 is a schematic view of a photomask for forming the patterned Raman detecting chip (1) as disclosed in Example 10.
Figure 17:
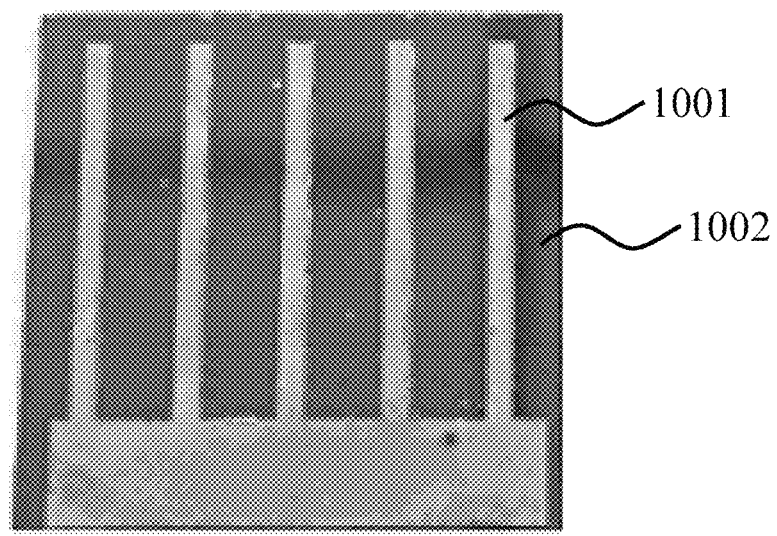
FIG. 17 is a schematic view of the patterned Raman detecting chip (1) as disclosed in Example 10.

First, a single-crystalline silicon chip (15 mm×25 mm) was provided. Next, a photoresist layer (manufactured and sold by Everlight Electronics Co. with a trade number of EPG-516) with a thickness of was formed on the single-crystalline silicon chip. Next, the photoresist layer was exposed through the photomask as shown in FIG. 16. Next, a development process is performed with an aqueous potassium hydroxide (KOH) solution (1%) as developer solution, obtaining a patterned photoresist layer. Next, the single-crystalline silicon chip was immersed in a solution including silver nitrate ($AgNO_3$, with a concentration of 0.44M) and hydrofluoric acid (HF, with a concentration of 4.6M) for a first time period (about 10 seconds). Next, after the single-crystalline silicon chip was removed from the solution including silver nitrate and hydrofluoric acid, the single-crystalline silicon chip was immersed in a solution including hydrofluoric acid (HF, with a concentration of 4.6M) and hydrogen peroxide ($H_2O_2$, with a concentration of 0.44M) for a second time period (about 4 minutes), such that the single-crystalline silicon chip was subjected to a metal assisted chemical etching (MACE) process. Thus, a silicon substrate having a plurality of silicon nanowires was obtained, wherein the average length of the silicon nanowires was of about 1 μm. Next, the silicon substrate was immersed in a solution including silver nitrate ($AgNO_3$, with a concentration of 0.01M) for a third time period (about 120 seconds), and then a silver particle layer was formed to cover the top surface and a part of the side wall of the silicon nanowire. Therefore, Patterned Raman detecting chip (1) with a plurality of strip-shaped regions (with a width of 1 mm and a length of 11 mm) was obtained, as shown in FIG. 17. In particular, the silicon nanowires were within the strip-shaped regions.

The first portion 1001 (having silicon nanowires disposed thereon) and the second portion 1002 (having no silicon nanowires disposed thereon) were subjected to the water contact angle measurement. The results show that the first portion 1001 has a water contact angle of 6 degree, and the second portion 1001 has a water contact angle of 70 degree. Accordingly, the hydrophilicity of first portion 1001 (having silicon nanowires disposed thereon) is particularly distinct from that of the second portion 1002 (having no silicon nanowires disposed thereon). The hydrophilicity difference causes the confinement effect, thereby confining the analyte in the first portion (having silicon nanowires disposed thereon).

Example 11

Figure 18:
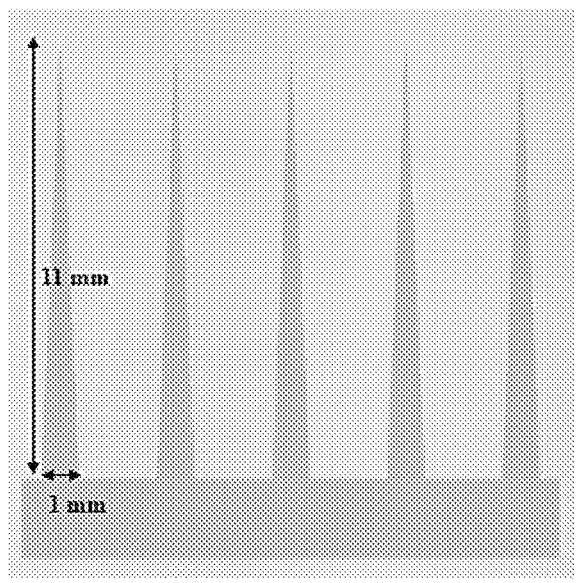
FIG. 18 is a schematic view of a photomask for forming the patterned Raman detecting chip (2) as disclosed in Example 11.
Figure 19:
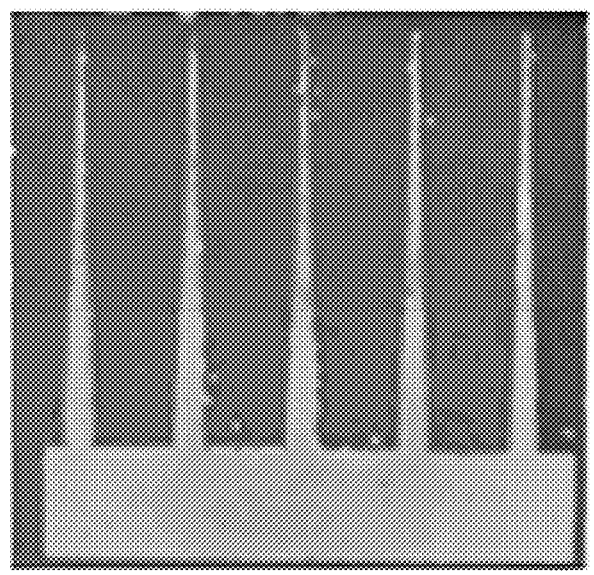
FIG. 19 is a schematic view of the patterned Raman detecting chip (2) as disclosed in Example 11.

Example 11 was performed in the same manner as in Example 10 except that the photomask as shown in FIG. 16 was replaced with the photomask as shown in FIG. 18, obtaining patterned Raman detecting chip (2) with a plurality of triangle-shaped regions (with a height of 11 mm), as shown in FIG. 19.

Example 12

Figure 20:
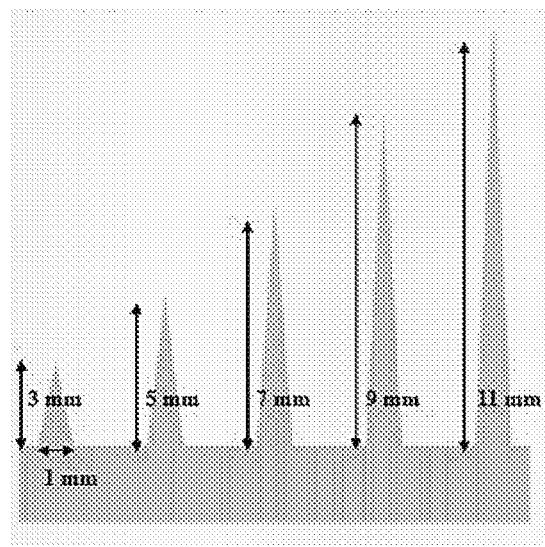
FIG. 20 is a schematic view of a photomask for forming the patterned Raman detecting chip (3) as disclosed in Example 12.
Figure 21:
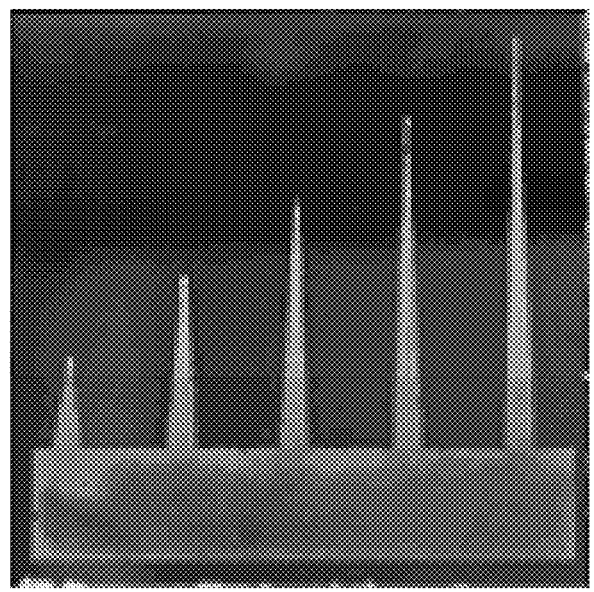
FIG. 21 is a schematic view of the patterned Raman detecting chip (3) as disclosed in Example 12.

Example 12 was performed in the same manner as in Example 10 except that the photomask as shown in FIG. 16 was replaced with the photomask as shown in FIG. 20, obtaining patterned Raman detecting chip (3) with a plurality of triangle-shaped regions (with different height), as shown in FIG. 21.

Detection and Separation by Means of Patterned Raman Detecting Chips

Example 13

First, a solution including rhodamine 6G (with a concentration of 10-4M) (henceforth referred to as R6G), a solution including methylene blue (with a concentration of 10-4M) (henceforth referred to as MB), and a solution including rhodamine 6G and methylene blue (with a concentration of 10-4M, the ratio between rhodamine 6G and methylene blue is 1:1) (henceforth referred to as MIX) were provided as samples.

Figure 22:
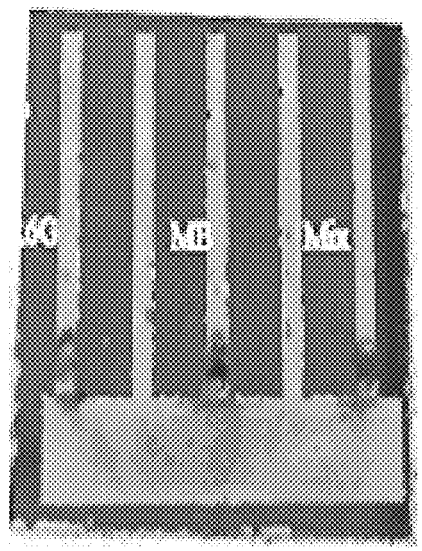
FIG. 22 is a schematic view of the patterned Raman detecting chip (1) after spotting a sample thereon as disclosed in Example 13.

Next, the solutions R6G, MB and MIX were applied to Patterned Raman detecting chip (1) with the Camag Linomat 5 sample applicator via air pressure to form sample points, as shown in FIG. 22. Next, the sample points were analyzed via surface enhanced Raman scattering spectroscopy, and the result is shown in FIG. 23.

Figure 23:
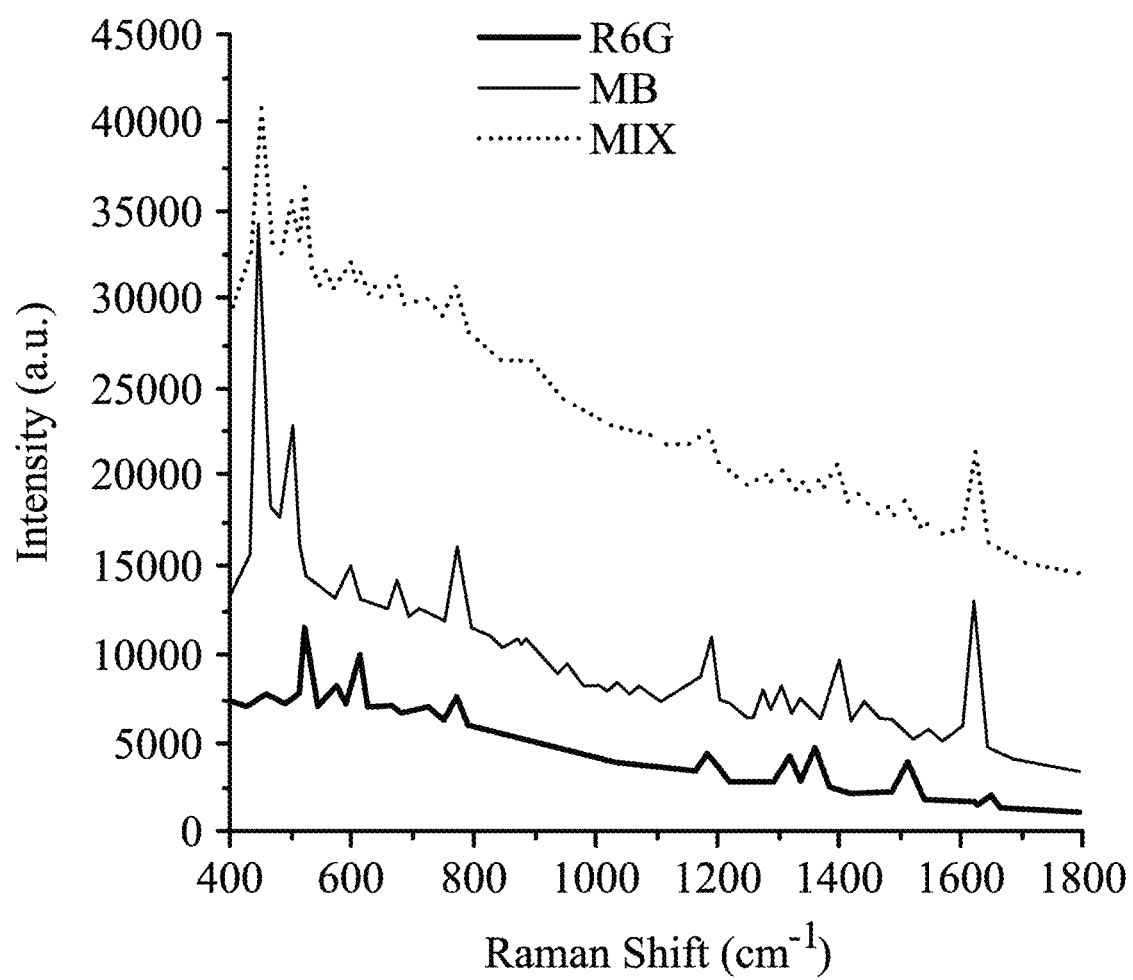
FIG. 23 is a Raman spectrum for detecting surface enhanced Raman scattering spectroscopy employing the Raman detecting chip (1) before performing the thin layer chromatography process as disclosed in Example 13.

As shown in FIG. 23, in comparison with the sample point of R6G, the sample point of MIX had a lower Raman scattering rhodamine 6G signal strength (1511 cm$^{-1}$). Similarly, in comparison with the sample point of MB, the sample point of MIX had a lower Raman scattering methylene blue signal strength (1625 cm$^{-1}$). It means that the rhodamine 6G signal strength (or methylene blue) in MIX was reduced due to the mutual interference.

Figure 24:
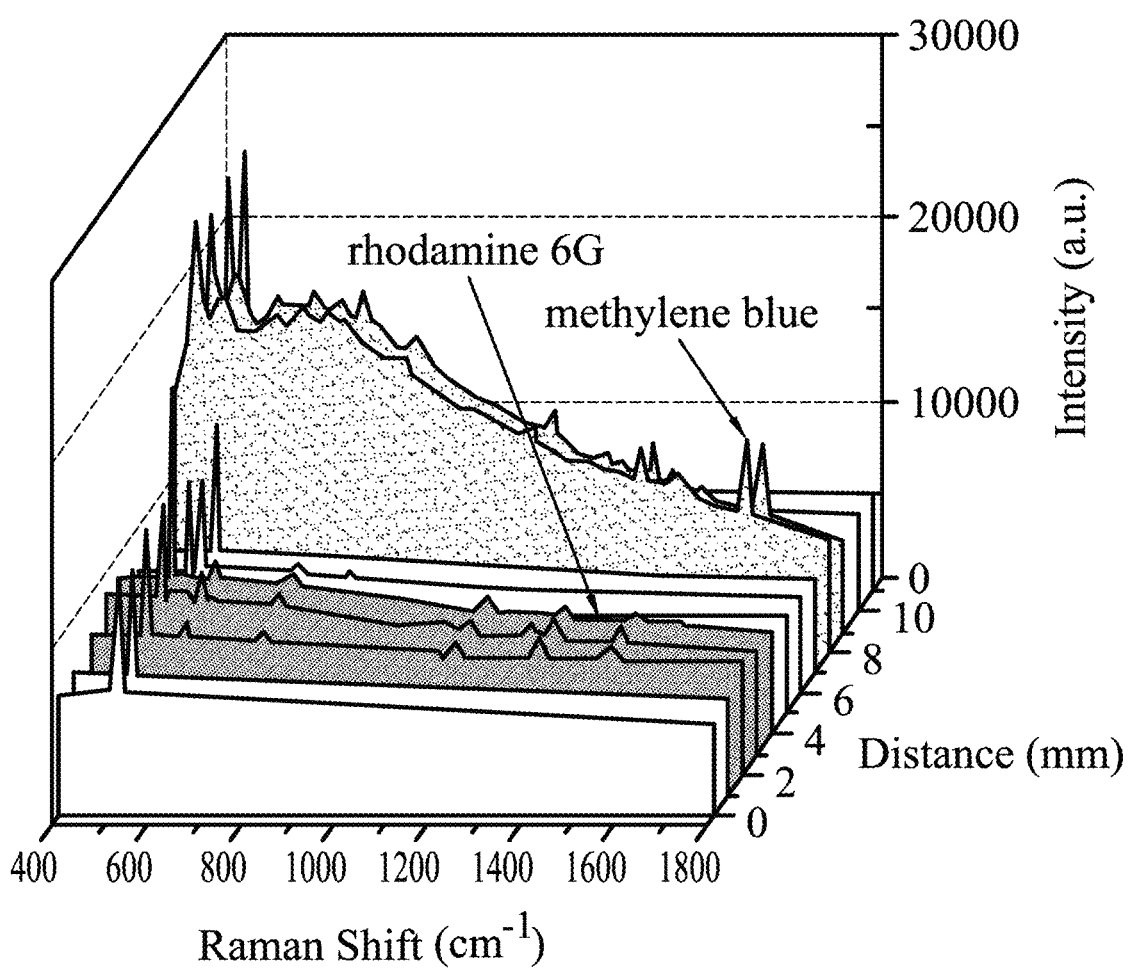
FIG. 24 is a Raman spectrum for detecting surface enhanced Raman scattering spectroscopy employing the Raman detecting chip (1) after performing the thin layer chromatography process as disclosed in Example 13.

Next, Patterned Raman detecting chip (1) was disposed in a developing tank with ethyl acetate serving as a developing solution. After developing, the signal strength of several analysis spots (separated by an interval of 1 mm) arranged in the developing direction of Patterned Raman detecting chip (1) were determined by surface enhanced Raman scattering spectroscopy. As a result, the distance from the analysis spot, which had the maximum rhodamine 6G signal strength, to the sample point was about 3 mm, and the distance from the analysis spot, which had the maximum signal strength of methylene blue, to the sample point was about 8 mm, as shown in FIG. 24. It means that the specific compound can be separated from the mixture by means of Patterned Raman detecting chip (1) of the disclosure.

Example 14

The solution including rhodamine 6G and methylene blue (MIX) as disclosed in Example 13 was provided. Next, the solution MIX was applied to Patterned Raman detecting chip (1), Patterned Raman detecting chip (2), and Patterned Raman detecting chip (3) (in the base region contacting the triangle-shaped region with a height of 9 mm) with the Camag Linomat 5 sample applicator via air pressure individually to form sample points. Next, Patterned Raman detecting chip (1), Patterned Raman detecting chip (2), and Patterned Raman detecting chip (3) were disposed in a developing tank with ethyl acetate serving as a developing solution. After developing, the methylene blue signal strength (1625 cm$^{-1}$) of the analysis spot, which was 8 mm away from the sample point (arranged in the developing direction), of Patterned Raman detecting chip (1), Patterned Raman detecting chip (2), and Patterned Raman detecting chip (3) were determined by surface enhanced Raman scattering spectroscopy. The results were shown in Table 2.

TABLE 2

| | Methylene blue signal strength (counts/s) |
|---|---|
| Raman detecting chip (1) | 780 |
| Patterned Raman detecting chip (1) | 2211 |
| Patterned Raman detecting chip (2) | 9273 |
| Patterned Raman detecting chip (3) | 12029 |

Figure 25:
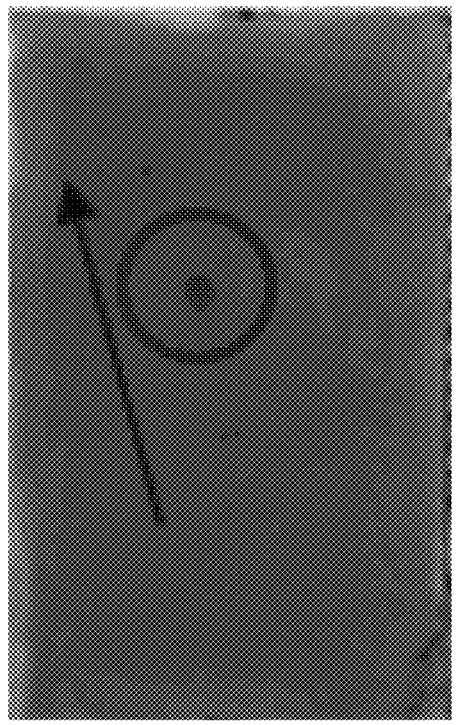
FIG. 25 is a schematic view of Raman detecting chip (1) after separating the sample by the thin layer chromatography process as disclosed in Example 14.

FIG. 25 is a schematic view of Raman detecting chip (1) after separating the sample by the thin layer chromatography process. Since Raman detecting chip (1) was not patterned, the developing direction of methylene blue slightly deviated from the developing direction of the developer solution. Due to the random drift of methylene blue, the methylene blue signal strength of Raman detecting chip (1) was 780 counts/s. Since Patterned Raman detecting chip (1) had strip-shaped regions severing as the pathway for developing methylene blue, methylene blue could be confined in the strip-shaped region (with a length of 11 mm). As a result, the methylene blue signal strength of Patterned Raman detecting chip (1) was increased to 2211 counts/s. Furthermore, in comparison with Patterned Raman detecting chip (1), since Patterned Raman detecting chip (2) had triangle-shaped regions (with a length of 11 mm), the triangle-shaped region further centralized methylene blue. Therefore, the methylene blue signal strength of Patterned Raman detecting chip (2) was obviously increased to 9273 counts/s. Furthermore, the height of the triangle-shaped region of Patterned Raman detecting chip (3) used for developing methylene blue was 9 mm. Since the analysis spot (8 mm away from the sample spot), which had the maximum methylene blue signal strength, was closer to the vertex of the triangle-shaped region having a height of 9 mm than the vertex of the triangle-shaped region having a height of 11 mm, a greater confinement effect was caused in Patterned Raman detecting chip (3). Therefore, the methylene blue signal strength of Patterned Raman detecting chip (2) was obviously increased to 12029 counts/s. The methylene blue signal strength observed in Patterned Raman detecting chip (3) is 15.42 times more than the methylene blue signal strength observed in Raman detecting chip (1).

It will be clear that various modifications and variations can be made to the disclosed methods and materials. It is intended that the specification and examples be considered as exemplary only, with the true scope of the disclosure being indicated by the following claims and their equivalents.

What is claimed is:

1. A Raman detecting chip for thin layer chromatography, comprising:
    a silicon substrate comprising a first portion, a second portion and a plurality of silicon nanowires disposed on the first portion, wherein each silicon nanowire has a top surface and a sidewall, and wherein the first portion comprises a plurality of regions and the plurality of regions have different surface areas; and
    a metal layer covering the top surface and at least a part of the sidewall of the silicon nanowire, wherein the silicon nanowire has a length L from 5 μm to 15 μm.

2. The Raman detecting chip for thin layer chromatography as claimed in claim 1, wherein the metal layer consists of a plurality of metal particles and has a thickness from 20 nm to 100 nm.

3. The Raman detecting chip for thin layer chromatography as claimed in claim 1, wherein a material of the metal particles is silver, gold, aluminum, copper, tin, titanium, barium, platinum, cobalt, or a combination thereof.

4. The Raman detecting chip for thin layer chromatography as claimed in claim 1, wherein the top surface of the silicon nanowire has a diameter from 50 nm to 200 nm, and the distance between two adjacent silicon nanowires is from 50 nm to 200 nm.

5. The Raman detecting chip for thin layer chromatography as claimed in claim 1, wherein the ratio between the length L1 of the side wall covered by the metal layer and the length L of the silicon nanowire is from 0.2 to 0.8.

6. The Raman detecting chip for thin layer chromatography as claimed in claim 1, wherein the ratio between the length L1 of the side wall covered by the metal layer and the length L of the silicon nanowire is from 0.3 to 0.74.

7. The Raman detecting chip for thin layer chromatography as claimed in claim 1, further comprising:
    a modification layer disposed on the side wall of the silicon nanowire which is not covered by the metal layer, wherein the modification layer is silicon oxide, silicon nitride, aluminum oxide, or a functional modification material which adjusts polarity of the silicon nanowire.

8. The Raman detecting chip for thin layer chromatography as claimed in claim 1, wherein the plurality of regions are a plurality of strip-shaped regions which have longitudinal axes parallel to each other, or a plurality of triangle-shaped regions.

9. A method for separating and detecting an analyte, comprising:
    providing the Raman detecting chip for thin layer chromatography as claimed in claim 1;
    providing a sample, wherein the sample comprises a solvent and at least one compound;
    spotting the sample on the Raman detecting chip for thin layer chromatography as claimed in claim 1;
    separating the sample by a thin layer chromatography process to obtain at least one analysis spot; and
    analyzing the analysis spot via surface enhanced Raman scattering spectroscopy.

* * * * *